United States Patent
Decourcy

(10) Patent No.: US 10,112,885 B2
(45) Date of Patent: Oct. 30, 2018

(54) PROCESS AND SYSTEM FOR PRODUCING ACRYLIC ACID

(71) Applicant: Arkema Inc., King of Prussia, PA (US)

(72) Inventor: Michael S. Decourcy, Houston, TX (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 15/118,126

(22) PCT Filed: Feb. 12, 2015

(86) PCT No.: PCT/US2015/015520
§ 371 (c)(1),
(2) Date: Aug. 11, 2016

(87) PCT Pub. No.: WO2015/126704
PCT Pub. Date: Aug. 27, 2015

(65) Prior Publication Data
US 2017/0174604 A1    Jun. 22, 2017

Related U.S. Application Data

(60) Provisional application No. 61/942,261, filed on Feb. 20, 2014.

(51) Int. Cl.
| | | |
|---|---|---|
| *C07C 51/44* | (2006.01) | |
| *C07C 51/42* | (2006.01) | |
| *B01D 3/10* | (2006.01) | |
| *B01D 3/14* | (2006.01) | |
| *B01D 5/00* | (2006.01) | |

(52) U.S. Cl.
CPC .............. *C07C 51/44* (2013.01); *B01D 3/10* (2013.01); *B01D 3/14* (2013.01); *B01D 5/006* (2013.01); *B01D 5/0027* (2013.01); *C07C 51/42* (2013.01)

(58) Field of Classification Search
CPC ......... C07C 51/44; C07C 57/04; C07C 51/42; B01D 3/10; B01D 3/14; B01D 5/006; B01D 5/0027
See application file for complete search history.

(56) References Cited

U.S. PATENT DOCUMENTS

| | | | | |
|---|---|---|---|---|
| 3,168,136 | A * | 2/1965 | Ammon | F28D 7/06 165/157 |
| 3,314,220 | A * | 4/1967 | Goldstein | B01D 45/16 122/34 |
| 5,980,698 | A * | 11/1999 | Abrosimov | B01D 3/10 196/114 |
| 6,019,820 | A | 2/2000 | Leverett | |
| 6,423,875 | B1 * | 7/2002 | Machhammer | C07C 45/33 562/532 |
| 6,525,216 | B1 * | 2/2003 | Nishimura | B01D 3/009 422/198 |
| 6,596,129 | B1 | 7/2003 | Yoneda et al. | |
| 6,677,482 | B2 | 1/2004 | Nishimura et al. | |
| 6,878,239 | B1 * | 4/2005 | Matsumoto | C07B 63/04 203/100 |
| 7,288,169 | B2 | 10/2007 | Yada et al. | |
| 8,242,308 | B2 | 8/2012 | Ho et al. | |
| 2011/0213174 | A1 | 9/2011 | Dubois | |
| 2012/0108767 | A1 * | 5/2012 | Devaux | C07C 45/52 526/75 |
| 2012/0226074 | A1 * | 9/2012 | Ho | C07C 51/44 562/600 |

FOREIGN PATENT DOCUMENTS

| | | | |
|---|---|---|---|
| EP | 0557790 | * | 9/1993 |
| WO | WO 2009/123872 A1 | | 10/2009 |
| WO | WO 2010/027732 A1 | | 3/2010 |

* cited by examiner

*Primary Examiner* — Yevgeny Valenrod
*Assistant Examiner* — Blaine G Doletski
(74) *Attorney, Agent, or Firm* — Lynn B. Morreale

(57) ABSTRACT

A process for recovering (meth)acrylic acid includes distilling a mixture comprising (meth)acrylic acid in a finishing column at less than atmospheric pressure to produce a finishing column overhead stream and a finishing column bottoms stream. An overhead aspirating direct contact condenser system at least partially condenses the finishing column overhead stream to form a finishing column overhead condensate and an overhead non-condensables vent stream. A finishing column vapor-phase side draw may also be recovered. An aspirating direct contact condenser system may be used to at least partially condense the vapor-phase side draw.

23 Claims, 3 Drawing Sheets

PROCESS AND SYSTEM FOR PRODUCING ACRYLIC ACID

CROSS-REFERENCE TO RELATED APPLICATIONS

This application is a national stage application under 35 U.S.C. § 371 of PCT/US2015/015520 filed Feb. 12, 2015, which claims benefit to U.S. patent application 61/942,261, filed Feb. 20, 2014.

BACKGROUND OF THE INVENTION

The great majority of acrylic acid produced commercially is prepared via the catalytic, two-stage vapor phase oxidation of propylene. In the first stage propylene is oxidized with air to acrolein and then fed directly to the second stage where the acrolein is further oxidized with air to acrylic acid. The catalysts used in the two stages are mixed metal oxides that have been optimized for their respective chemistries. The first stage catalyst is composed of mainly molybdenum and bismuth oxides with several other metals. The second stage catalyst is also a complex mixed metal oxide catalyst where the oxides employed are primarily of molybdenum and vanadium. Several other components have been incorporated in the catalyst to optimize activity and selectivity. Acrylic acid yields of 80-90% from propylene have been realized for these commercial catalyst systems.

Downstream of the oxidation reactors, additional processing steps are utilized to cool, collect, and purify acrylic acid present in the reactor exit gas stream. The original acrylic acid processes used water as the diluent, which meant that the reactor product yielded an approximately 35% aqueous acrylic acid solution upon quenching and separation of the non-condensable gases in the quench or absorber tower. This low concentration of acrylic acid in water had to be recovered via a solvent based extraction followed by several distillation steps to generate a technical grade acrylic acid. Technical grade acrylic acid is used to prepare the higher purity glacial acrylic acid or to prepare acrylates, i.e., esters of acrylic acid. When recycle gas technology was introduced, the aqueous acrylic acid obtained in the quench tower was concentrated to approximately 65% which allowed the use of solvent-based azeotropic distillation to remove the water. The crude acrylic acid after water removal was then subjected to several distillation steps to yield a technical grade acrylic acid. An alternate technology for recovery of the 65% aqueous acrylic acid involves the introduction of a high boiling solvent in the quench tower to absorb the acrylic acid via a solvent swap. The base of the quench tower yields acrylic acid dissolved in this high boiling solvent instead of water. The acrylic acid is then subjected to further distillation steps for recovery from the high boiling solvent to yield technical grade acrylic acid.

U.S. Pat. No. 6,596,129 teaches using two condensers in series in a (meth)acrylic acid distillation process.

U.S. Pat. No. 6,878,239 teaches the addition of an inhibitor to a steam jet ejector condensate, surface condensers, and a liquid ring ("nash") vacuum pump to prevent polymer formation. The vacuum section is a separate system from the overhead condensers.

U.S. Pat. No. 5,980,698 discloses a distillation column to produce vacuum gas oil in a separation process using a cooled product stream entering the separator.

U.S. Pat. No. 6,019,820 teaches the use of a liquid jet eductor as a gas compression system supplied with high pressure liquid to increase the gas outlet pressure.

Conventional processes for producing acrylic acid generally add solvents in the distillation column or in the condensers. Additionally, water in the form of steam is often introduced through the use of steam jet ejectors, which help reduce the operating pressure within distillation columns. For example, U.S. Pat. No. 7,288,169 teaches the use of steam jet ejector-based vacuum systems for acrylic acid distillation columns. The systems disclosed by U.S. Pat. No. 7,288,169 comprise vertical shell-and-tube surface condensers, steam jet ejectors, and a steam jet condensate collection tank, which is used to collect and recycle the steam jet condensate.

U.S. Pat. No. 6,677,482 teaches an improvement to the use of steam jet ejectors and surface condensers by recycling the condensed steam back into the separations process.

A schematic process flow sheet of a prior art configuration in which shell-and-tube condensers and steam jet ejectors condense the overhead product of a finishing column is shown in FIG. 2. In FIG. 2, finishing column overhead stream 8 is removed from finishing column 17 as a vapor and is passed through at least one vertical shell-and-tube surface condenser 19 to form a finishing column overhead condensate stream, at least a portion of which is passed, via line 4, to dehydration column heater/reboiler 12.

Reduced operating pressure within finishing column 17 is maintained in this prior art process through the use of a common multistage steam jet ejector vacuum system 50. Such a vacuum system is well known in the art and comprises a plurality of steam jet ejectors and associated interstage jet condensers. As illustrated in FIG. 2, steam is supplied to a first jet ejector 51, which draws organic vapors and non-condensable gases out of condenser 19 via line 25. The organic vapors and the steam are ejected into shell-and-tube surface condenser 52, where they are at least partially condensed, forming a first aqueous steam condensate stream 54, which further comprises condensed organics. Steam is also supplied to a second jet ejector 55, which draws residual organic vapors and non-condensable gases out of condenser 52 via line 53. The residual organic vapors and the steam are ejected into shell-and-tube surface condenser 56, where they are at least partially condensed, forming a second aqueous steam condensate stream 58, which further comprises condensed organics. Non-condensable gases and any remaining uncondensed organic vapors are vented from the vacuum system via vent line 57. Steam condensate streams 54 and 58 are collected in condensate receiver 59. Because the steam condensate in receiver 59 comprises condensed organics, aqueous stream 60 cannot be directly discharged to the environment and therefore requires additional processing. In some instances, it may be possible to transfer aqueous stream 60 to another separations system. In other embodiments, however, such a "recycling" option is not economically justified and stream 60 is instead transferred to an aqueous wastewater treatment system or even a thermal oxidizer for disposal.

An improved process for producing acrylic acid is disclosed in U.S. Pat. No. 8,242,308, which is incorporated in its entirety herein by reference. U.S. Pat. No. 8,242,308 discloses a process which does not require the addition of an azeotropic solvent or other solvent in the distillation columns, thus eliminating the need for additional purification of the acrylic acid product stream. WO 2009/123872 describes a method for starting up a (meth)acrylic acid production process of the type disclosed in U.S. Pat. No. 8,242,308.

It would be desirable to have an acrylic acid production process which eliminates or minimizes the generation of an aqueous waste stream and/or provides reduced capital and operation costs.

SUMMARY OF THE INVENTION

The present invention is such a recovery system, applicable to acrylic acid as well as methacrylic acid, which comprises a solvent-free distillation system for generation of acrylic acid. According to at least one embodiment, the recovery system does not produce an aqueous waste stream.

A first aspect of the present invention relates to a process for the recovery of (meth)acrylic acid comprising:
A. dehydrating a gaseous reaction mixture comprising (meth)acrylic acid in a dehydration column to produce a dehydration column overhead stream and a dehydration column bottoms stream;
B. passing at least a portion of the dehydration column bottoms stream to the upper half of a finishing column;
C. subjecting the portion of the bottoms stream passed to the finishing column to distillation at less than atmospheric pressure within the finishing column to produce at least a finishing column overhead stream and a finishing column bottoms stream;
D. at least partially condensing the finishing column overhead stream using an overhead aspirating direct contact (ADC) condenser system to form a finishing column overhead condensate, and passing at least a portion of the finishing column overhead condensate to the dehydration column; and
E. collecting (meth)acrylic acid from the finishing column.

In at least one embodiment, a vapor-phase side draw product stream is recovered from the finishing column. In at least one further embodiment, the vapor-phase side draw product stream is at least partially condensed by an aspirating direct contact (ADC) condenser system.

Another aspect of the present invention relates to a process comprising:
A. forming a gaseous reaction mixture comprising (meth)acrylic acid through the gas-phase oxidation of at least one (meth)acrylic acid precursor;
B. cooling the gaseous reaction mixture;
C. dehydrating the cooled gas mixture in a dehydration column to produce a dehydration column overhead stream and a dehydration column bottoms stream, wherein the dehydrating is carried out without using an azeotropic solvent;
D. at least partially condensing the dehydration column overhead stream to form a condensate, and returning at least a portion of the condensate to the dehydration column as reflux;
E. dividing the dehydration column bottoms stream into at least first and second dehydration column bottom streams, and passing at least a portion of one of the first and second dehydration column bottoms stream to a dehydration column heater/reboiler and passing at least a portion of the other dehydration column bottoms stream to the upper half of a finishing column;
F. subjecting the portion of the bottoms stream passed to the finishing column to distillation at less than atmospheric pressure within the finishing column to produce at least a finishing column overhead stream and a finishing column bottoms stream comprising heavy components;
G. at least partially condensing the finishing column overhead stream using an overhead aspirating direct contact (ADC) condenser system to form a finishing column overhead condensate and an overhead aspirating direct contact condenser system non-condensables vent stream, and passing at least a portion of the finishing column overhead condensate to the dehydration column heater/reboiler; and
H. passing at least a portion of the finishing column bottoms stream to a finishing column heater/reboiler.

In another aspect of the present invention, an apparatus for producing (meth)acrylic acid is provided which comprises:
A. a dehydration column;
B. a finishing column, wherein the dehydration column is in fluidic communication with the finishing column and at least a portion of a dehydration column bottoms stream is withdrawn from the dehydration column and fed to the finishing column; and
C. at least one aspirating direct contact condenser system connected to the finishing column to condense a stream chosen from a finishing column overhead stream and a finishing column side stream.

Surprisingly, the process of the invention can produce technical grade acrylic acid without producing a wastewater stream. Eliminating the wastewater stream results in lower capital expenditures and reduced operating costs. Advantageously, the process of the invention does not require a solvent, which also leads to reduced operational costs.

DETAILED DESCRIPTION OF THE INVENTION

Figure 1:
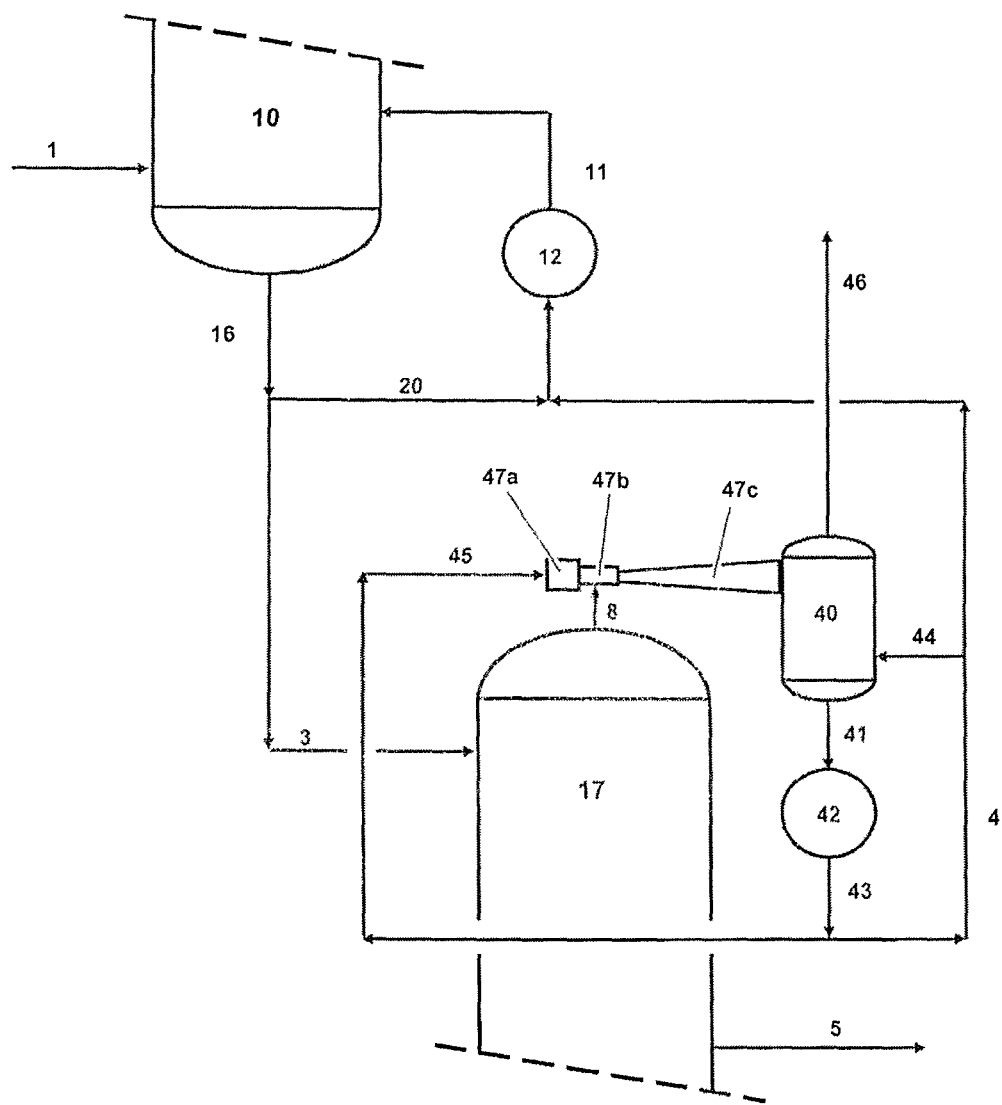
FIG. 1 is a schematic process flow sheet showing a configuration in which an aspirating direct contact condensing system condenses the overhead stream of a finishing column.
Figure 2:
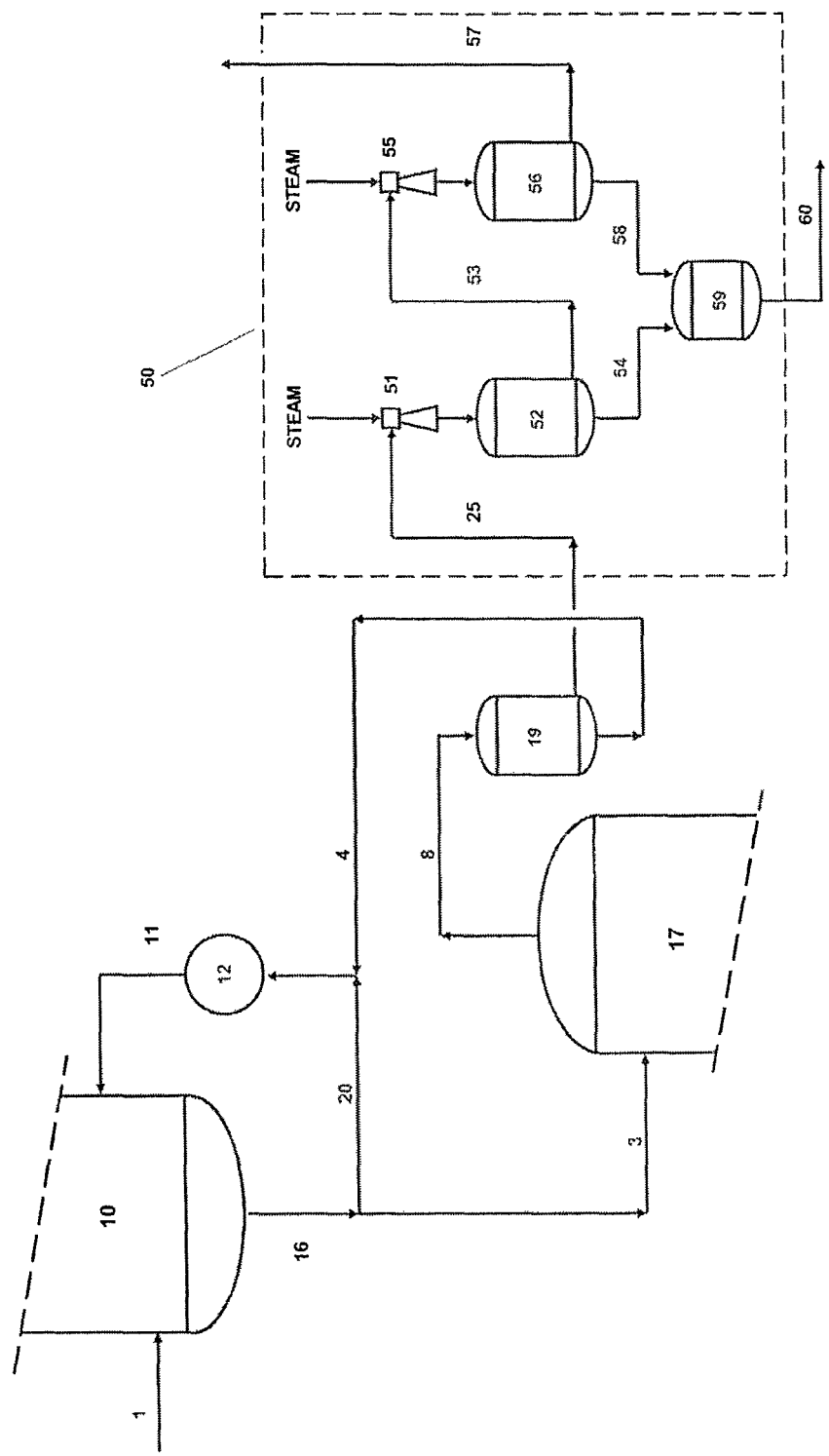
FIG. 2 is a schematic process flow sheet showing a prior art configuration in which shell-and-tube surface condensers and steam jet ejectors condense the overhead stream of a finishing column.

The numerical ranges in this disclosure include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, temperature, pressure, equipment sizes, relative amounts of components in mixtures and/or blends, and the like.

The term "(meth)" indicates that the methyl substituted compound is included in the term. For example, the term (meth)acrylic acid represents either acrylic acid or methacrylic acid. Similarly, the term "(meth)acrolein" indicates either acrolein or methacrolein.

For the purposes of the invention, the terms "light" and "light compound" and their plurals refer to a compound or compounds having a boiling point or boiling points below the boiling point of the desired product. For example, water is an example of a light compound when the desired product is acrylic acid. A lights stream contains at least one light compound.

Similarly, the term "heavies" for the purposes of the invention means compounds having a boiling point above the boiling point of the desired product. Oligomers of acrylic acid and well known Michael addition products are examples of heavies when the desired product is acrylic acid.

The term "separation system" refers to the equipment comprising a dehydration column and a second column, as are described herein, used in the process of the invention.

The term "technical grade acrylic acid" refers to an acrylic acid that contains at least 98.5% acrylic acid by weight, preferably contains at least 99% acrylic acid, and more preferably at least 99.5% acrylic acid. Furthermore the acrylic acid contains less than 0.5% water and less than 0.4% acetic acid, preferably contains less than 0.3% water and less than 0.2% acetic acid, and more preferably contains less than 0.15% water and less than 0.075% acetic acid.

The term "coupled distillation columns" refers to two distillation columns connected in a manner such that the tails stream from the first column is fed directly or indirectly into the top of the second column while the overhead stream of the second column is fed directly or indirectly into the base of the first column. "Indirectly" means that the stream first passes through at least one other vessel, e.g., a surge tank and/or heat exchanger, before entering the first or second column.

The term "dewpoint" refers to the temperature, measured at atmospheric pressure, at which the first droplet of liquid condenses from a vapor stream.

The interchangeable terms "non-condensable gases" and "non-condensables" is meant gases with a dewpoint of less than 0° C. (less than 32° F.). Examples of non-condensable gases include but are not limited to nitrogen, oxygen, and argon. Such non-condensable gases may be present in the process as a result of adding oxygen-containing gas to the finishing column in order to inhibit polymerization within the column.

The term "subcooling" refers to cooling a liquid stream to a temperature of at least 0.5° C. (0.9° F.) below its dewpoint. Similarly, the term "subcooler" indicates a heat exchanger which provides subcooling of a liquid stream passed therethrough.

The term "direct contact condenser" refers to a condenser in which a cooling liquid stream is intimately mixed with a vapor stream to cause condensation of at least a portion of said vapor stream.

The term "surface condenser" refers to a condenser in which a cooling liquid stream is used to cool an intermediate surface, and said cooled intermediate surface is then used to cause condensation of at least a portion of a vapor stream; in such a condenser, the intermediate surface typically prevents the cooling liquid from being intimately mixed with the vapor stream. Shell-and-tube heat exchangers are a common example of a surface condenser and the tubes within a shell-and-tube heat exchanger are the intermediate surface.

One aspect of the present disclosure relates to the use of aspirating direct contact (ADC) condensers in a process for producing acrylic acid. In accordance with at least one embodiment, the ADC condensers are used in a solvent-free process such as that disclosed in U.S. Pat. No. 8,242,308, which is described below and shown schematically in FIG. 3.

The feed stream to the process of the invention preferably is a gaseous reaction mixture comprising (meth)acrylic acid. Preferably, this mixture results from the two-step catalytic vapor phase oxidation of at least one (meth)acrylic acid precursor, such as propylene in the case of acrylic acid or isobutylene in the case of methacrylic acid. The second step of the oxidation process typically converts an intermediate, such as (meth)acrolein, to the final product. See U.S. Pat. No. 6,646,161 B1, the teachings of which are incorporated herein by reference, for a discussion the composition of the hot gaseous reaction mixture. Alternatively, acrylic acid may be produced by the catalytic vapor phase oxydehydrogenation of propane to form acrolein, which is in turn oxidized to form acrylic acid.

Methacrylic acid may be produced similarly. For example, methacrolein may be produced via the oxidation of isobutylene and/or tert-butanol or via the oxydehydrogenation of butane and/or isobutane. Methacrolein may then be oxidized to form methacrylic acid.

Alternatively, the gaseous reaction mixture may be produced by the dehydration of renewable or bio-materials, such as, for example, glycerol, 3-hydroxypropionic acid (3-HP), and 2-hydroxy propanoic acid (lactic acid). For example, glycerol may be catalytically dehydrated to form acrolein, which is subsequently oxidized to form acrylic acid. One process for producing bio-resourced acrylic acid from glycerol is disclosed in U.S. Patent Application Publication No. 2012/0108767, which is incorporated herein by reference. Another process for producing (meth)acrylic acid is disclosed in French Patent Application No. 1451315, filed Feb. 19, 2014 (Arkema Ref: AM 3243 FR), which is incorporated herein by reference in its entirety.

In the process of the invention, the gaseous reaction mixture is dehydrated in a first column, which is known as a dehydration column or tower. The dehydration column functions to remove the majority of water from the incoming gaseous reaction mixture. Advantageously, the dehydration column is operated such that there is a bottoms stream and an overhead stream. Preferably, at least a portion of the overhead stream is condensed and is returned as a reflux liquid to the dehydration column.

Preferably, the pressure in the dehydration column is no higher than the pressure of the incoming gaseous reaction mixture. It is also preferred that the temperature of the bottoms stream from the dehydration column is less than about 120° C. The temperature of the overhead stream from the dehydration column preferably is at least about 40° C. In one embodiment of the invention, essentially all non-condensables and lights exit the dehydration column in the overhead stream. Examples of non-condensables present during the production of acrylic acid include, for example, nitrogen, oxygen, carbon monoxide, carbon dioxide, and unreacted hydrocarbons such as propane and propylene. Advantageously, the entire overhead stream is introduced into a condenser, and at least a portion of the lights are condensed and returned to the dehydration column as a reflux stream.

According to at least one embodiment, an azeotropic solvent is not added to the dehydration column.

The bottoms stream from the dehydration column advantageously is sent to a second column (also referred to as a finishing column or tower), except that a portion of this stream can be employed to cool the gaseous reaction mixture. In one embodiment of the invention, a portion of the bottoms stream from the dehydration column is sent to a heat exchanger, which can be a reboiler. However, it is noted that the process can also be operated under conditions such that the heat exchanger is a cooler, depending on whether the process design requires heating or cooling. In a preferred embodiment of the invention, a portion of the bottoms stream from the dehydration column is fed to the finishing column. Advantageously, the feed point is the top of the finishing column. The finishing column preferably is a distillation column and is used in conjunction with a reboiler and a condenser.

The finishing column has an overhead stream and two product streams, i.e., a side stream and a residue stream. The difference between these streams is the heavy ends content. The two key heavy end components in these streams are the acrylic acid dimer, i.e., Michael addition product, and maleic acid/anhydride. As the take-off ratio of side stream to residue stream increases, these heavy ends concentrate in the residue stream relative to the side stream. The residue stream (sometimes referred to as ester grade acrylic acid) is typically unsuitable as a feed to a melt crystallizer, i.e., a glacial acrylic acid unit, due to the high dimer, inhibitor and maleic acid/anhydride content.

The temperature and pressure in the finishing column are not particularly critical, and can be determined according to design considerations well-known to those skilled in the art. Preferably, the finishing column is operated below the operating pressure of the dehydration column. Preferably, the finishing column is operated at subatmospheric conditions. This has the advantage of allowing the finishing column to operate at lower temperatures, thereby minimizing undesired dimer, oligomer and/or polymer formation. Advantageously, the temperature of the overhead stream as it leaves the finishing column is from about 40 to about 90° C. when producing acrylic acid and operating the finishing column at a head pressure of from about 40 to about 500 mm Hg. In at least one embodiment, the finishing column is operated at a pressure of not more than 100 mm Hg. The temperature of the bottoms stream from the finishing column advantageously is from about 60 to about 120° C. when producing acrylic acid.

The finishing column of the present invention comprises at least one aspirating direct contact (ADC) condenser system. In a preferred embodiment, the overhead stream from the finishing column is sent to an ADC condenser system. An ADC condenser system uses a liquid jet eductor to generate a vacuum by passing a stream of liquid through a nozzle, which aspirates a vapor stream through a vapor suction port. The liquid and vapor are mixed within the suction port, and the vapor is at least partially condensed in an expansion section. Thus, the ADC can provide subatmospheric pressures to remove the light ends from the bottoms stream of the dehydration column.

Advantageously, an acrylic acid product stream is recovered from the finishing column as a side draw stream. The location of the side draw on the second column is a matter of design preference, and can be determined using design techniques well-known to those skilled in the art. The acrylic acid product is removed from the side of the distillation tower as predominantly a vapor or a liquid. In at least one embodiment of the present invention, the finishing column side draw stream comprises a vapor. According to at least one embodiment, an ADC condenser system may be used to withdraw the vapor side draw from the second column. In a further embodiment, the finishing column may comprise an overhead ADC condenser system and a side ADC condenser system.

The weight ratio of the side draw to bottom stream is preferably 75:25, or more preferably 95:5. However, advantageously, the side draw to bottom stream weight ratio can also be designed by one skilled in the art to be 25:75 or even 5:95. In a further embodiment, no side draw is taken and all the acrylic acid product is taken in the bottoms stream. As a practical matter, the side stream is typically of better quality than the tails, i.e., the side stream contains less heavy components than does the tails.

One surprising advantage of the process is that the product stream is produced in high purity by a process that does not require an azeotropic solvent or other solvent. For example, the product stream advantageously contains at least about 98.5% acrylic acid by weight, preferably contains at least about 99% acrylic acid, and more preferably at least about 99.5% acrylic acid. Advantageously the product stream contains less than about 0.5% water and less than about 0.4% acetic acid, preferably contains less than about 0.3% water and less than about 0.2% acetic acid, and more preferably contains less than about 0.15% water and less than about 0.075% acetic acid. The process of the invention preferably can produce a product stream that is usable as technical grade acrylic acid without further separation processing.

One or more near infrared (NIR) spectrometers may be used to monitor stream compositions (e.g., overhead stream, side draw stream, bottom stream) and/or to control operation of the process. Such NIR spectrometers are known in the art and have been disclosed, for example, in U.S. Patent Application Publication No. 2011/172462, which is incorporated herein by reference. In at least one embodiment, a NIR spectrometer monitors the overhead stream of the finishing column.

According to at least one embodiment, inhibitors are used to inhibit the reaction of acrylic acid. Examples of preferred inhibitors include soluble manganese ions, soluble copper ions, 2,2,6,6-tetramethyl-1-piperidinyloxy (TEMPO) and related compounds such as 4-hydroxy TEMPO (4HT), hydroquinone (HQ), monomethyl ether of hydroquinone (MeHQ), and phenothiazine (PTZ). Combinations of inhibitors can be employed. In a preferred embodiment of the invention, a mixture of a source of soluble manganese ions, such as manganese acetate, and 4-hydroxy TEMPO are employed in the dehydration column as an inhibitor. 4-hydroxy TEMPO/manganese acetate is also the preferred inhibitor for the finishing column. An alternate inhibitor system that could be used in both columns is hydroquinone/manganese acetate. It is also preferred, as is well-known in the art, to employ molecular oxygen or air to the finishing column, as oxygen is also known to be an inhibitor. The inhibitor is employed in an amount sufficient to prevent or reduce the polymerization of acrylic acid, as is well known to those skilled in the art. In the case of the current invention, air injection is only required for the finishing column because the reaction gases fed to the dehydrator already contain oxygen in an amount sufficient for the inhibitor system. Typically, sufficient air is injected such that oxygen is present in the column in an amount of at least 0.1 volume percent relative to the amount of vapor in the column.

The design details of the dehydration column and of the finishing column, including their operating conditions such as temperatures, pressures, flow rates, equipment sizing including column height and diameters, choice of materials of construction, arrangement and choice of type of auxiliary equipment such as heat exchangers and pumps, choice and arrangement of column internals, and location of piping including take-off streams, can readily be determined by those skilled in the art according to well-known design considerations.

Figure 3:
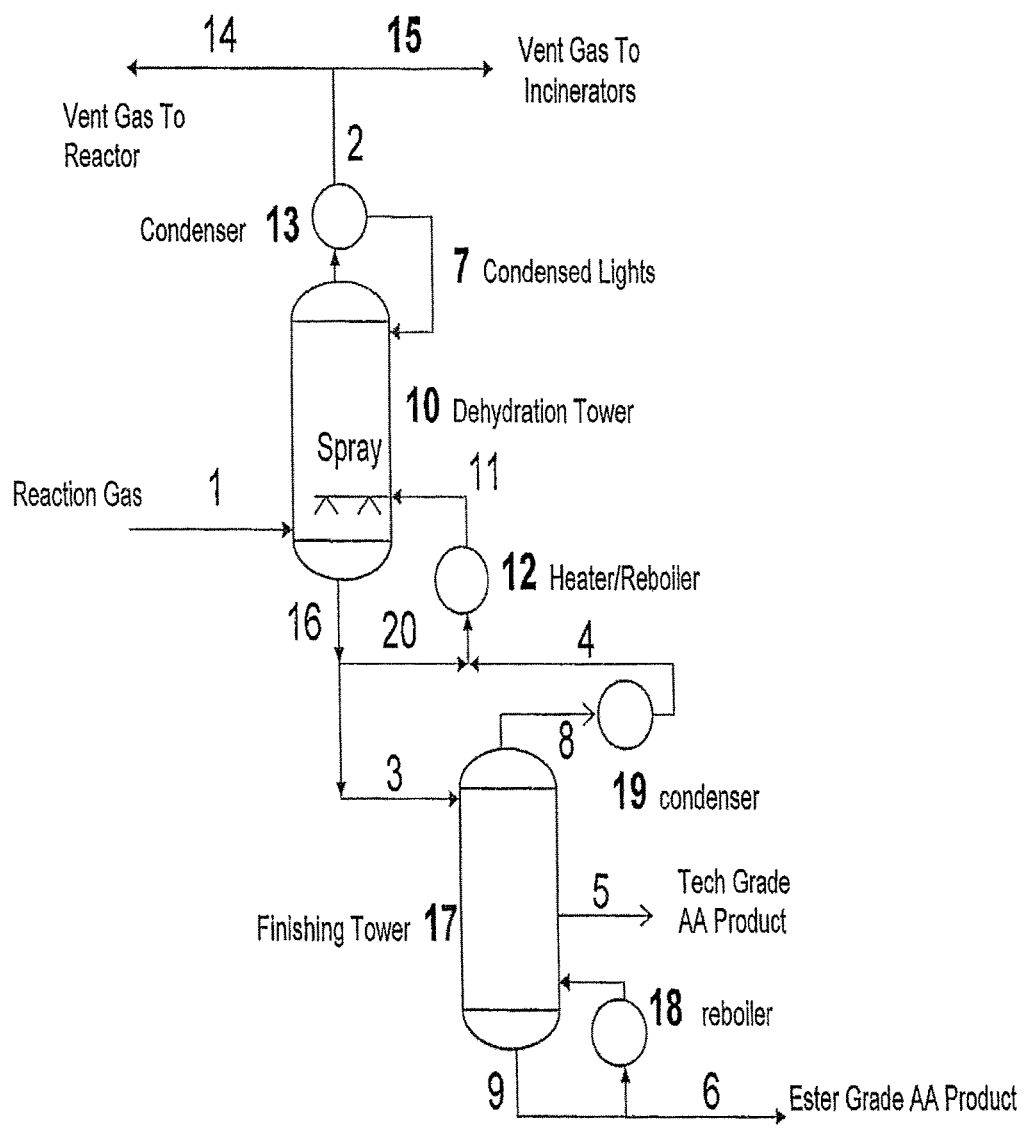
FIG. 3 is a schematic process flow sheet showing a process for producing and recovering acrylic acid.

One embodiment of an acrylic acid production system that may be used in accordance with the present invention is shown in FIG. 3. Referring to FIG. 3, hot reaction gas mixture feed stream 1 containing acrylic acid is introduced into the lower area of dehydration column (or tower) 10. Upon entering the dehydration column, the reaction gas mixture is contacted with, and cooled by, liquid 11 supplied from heat exchanger 12, which can be a cooler or a heater, but preferably is a reboiler. The contacting can comprise spraying, feeding the cooling liquid to a distillation tray or packing through which the hot reaction gaseous mixture rises, or a combination of these. The partially cooled gas mixture flows up the dehydration column through internals (not shown) which can be trays or packing of any configuration, as is well known to those skilled in the art. As the cooled gas mixture flows upward, it is contacted with a reflux liquid comprising condensed lights 7 from condenser 13. Gases and vapors that are not condensed in condenser 13 exit the condenser via condenser overhead stream 2, which is then split into recycle gas stream 14 and vent stream 15. Accordingly, the dehydration column functions to remove the majority of acrylic acid from reaction gas mixture feed stream 1, and to send the recovered acrylic acid via bottoms stream 16 for further treatment. Alternative configurations of the dehydration column may also be used, such as those disclosed in French Patent Application No. FR1357332, filed Jul. 25, 2013, which is hereby incorporated by reference in its entirety.

A portion of bottoms stream 16 from the dehydration column is fed to a point near the top of second column (or finishing column) 17 via second column feed stream 3. Another portion of bottoms stream 16 is fed to heat exchanger 12 via heat exchanger feed stream 20 and thus is recirculated to the dehydration column and is employed to cool the incoming hot reaction gas mixture. The liquid from second column feed stream 3 flows downward in the second column where it is contacted with rising vapors from reboiler 18. The second column preferably is a distillation column. The configuration of the distillation column is not particularly critical, and the column can be designed using criteria well known to those skilled in the art. Vapor phase overhead stream 8 from the second column is introduced into condenser 19, where the majority of the overhead stream is condensed. A small purge stream (not shown) of non-condensables passes out of condenser 19 as a vent stream, which can be disposed of, recycled, or otherwise handled. Condensed liquid from condenser 19 is sent via condensed liquid stream 4 to heat exchanger 12, and then is sent to the dehydration column via cooling liquid stream 11 to cool the gaseous reaction mixture of stream 1. A portion of second column bottoms stream 9 is recirculated to the second column via reboiler 18. The remainder of bottoms stream 9 flows via residual stream 6 for further treatment, disposal, or a combination of these. For example, residual stream 6 can be sent to an esters unit, to a cracking unit, or to a combination of these.

Acrylic acid product stream 5 is taken from the second column as a side draw. The stream preferably is a vapor stream, but can be a liquid stream.

In accordance with at least one embodiment, the condenser 19 comprises an ADC system, as shown in FIG. 1. The finishing column overhead ADC condenser system comprises at least one liquid jet eductor (comprising components 47a, 47b, and 47c), at least one liquid-vapor separatory vessel 40, and at least one condensate subcooler 42. In one embodiment, liquid-vapor separatory vessel 40 is a centrifugal separator.

In at least one embodiment, the overhead ADC condenser system may comprise at least one liquid jet eductor, at least one liquid-vapor separatory vessel, and at least one condensate cooler. In at least one further embodiment, the overhead ADC condenser system may comprise a plurality of liquid jet eductors, a plurality of liquid-vapor separatory vessels, and/or a plurality of condensate coolers. In embodiments in which the overhead ADC condenser system comprises a plurality of liquid jet eductors, a plurality of liquid-vapor separatory vessels, and/or a plurality of condensate coolers, the components may be connected in parallel or series.

In at least one embodiment, the overhead ADC condenser system comprises a plurality of liquid jet eductors operated in parallel. Each of the plurality of liquid jet eductors may draw suction on finishing column 17 at the same point and discharge into the same separatory vessel 40. Using a plurality of liquid jet eductors in parallel may allow for greater volumetric flow rates. Therefore, in larger columns with greater throughput, a plurality of liquid jet eductors may be used to provide adequate volumetric flow rates through the finishing column.

According to at least one embodiment, the overhead ADC condenser system may comprise a plurality of liquid jet eductors operated in series. For example, the first liquid jet eductor may draw vapor suction on finishing column 17 and discharge into separatory vessel 40, and a second liquid jet eductor may draw suction from vessel 40 and discharge into a second separatory vessel. Additional condensate coolers may also be used in conjunction with the liquid jet eductors and separatory vessels. Additional liquid jet eductors may be connected in series in the same manner. The use of liquid jet eductors in series may enable a greater vacuum to be pulled on finishing column 17. Because ADC systems use fewer pieces of process equipment than the prior art systems, capital investment costs may also be reduced.

In at least one embodiment, the ADC condenser system may further comprise one or more pumps, which may be optionally located in one or more of lines 41, 43, 44, 45, and 4. In at least one embodiment, at least one variable-speed centrifugal pump is located in line 41. Gas-buffered pump seals may be employed and the seal gas may comprise oxygen.

Within the finishing column overhead ADC condenser system, a liquid stream 45, comprising subcooled finishing column overhead condensate, is supplied to liquid jet eductor nozzle 47a. The flow of subcooled condensate through liquid jet eductor nozzle 47a aspirates finishing column overhead stream 8 through vapor suction port 47b. By way of the intimate mixing of the subcooled condensate and the finishing column overhead stream within port 47b and expansion section 47c, finishing column overhead stream 8 is at least partially condensed. The resulting mixture of subcooled condensate, liquid and vapor fractions of the finishing column overhead stream and optionally, oxygen-containing gas, is discharged into separatory vessel 40 to form a finishing column overhead condensate stream 41 and an overhead ADC condenser system non-condensables vent stream 46. In some embodiments, the flow rate of non-condensables vent stream 46 may be adjusted with an optional control valve (not shown) to regulate the pressure within separatory vessel 40.

In at least one embodiment, at least a portion of non-condensables vent stream 46 is transferred to dehydration column 10 (not shown). In at least one embodiment, at least a portion of non-condensables vent stream 46 may be transferred to a thermal oxidizer, a flare, or a catalytic combustion unit (not shown). Optionally, the transfer piping for non-condensables vent stream 46 may also include process safety equipment such as, for example, flame arrestors, composition analyzers, and pressure relief devices.

In accordance with at least one embodiment, at least a portion of non-condensables vent stream 46 is transferred to vapor suction port 47b to regulate pressure within finishing column 17. In an alternative embodiment, a controlled flow of oxygen-containing gas, such as for example atmospheric air or blend gas (for example, a blend comprising nitrogen and between 5 and 10% oxygen), may be provided to vapor suction port 47b to regulate pressure within finishing column 17.

Finishing column overhead condensate 41 may be removed from separatory vessel 40 and passed through at least one subcooler 42 to form subcooled finishing column overhead condensate stream 43. Subcooler 42 may comprise at least one heat exchanger selected from the list including: a shell-and-tube heat exchanger, a spiral heat exchanger, a monolithic block exchanger, a jacketed pipe, and a plate-and-frame heat exchanger. In at least one embodiment, subcooler 42 comprises at least one heat exchanger utilizing cooling tower water supplied at a temperature of between about 15° C. and 35° C. (59° F. and 95° F.) as the cooling medium. In another embodiment, subcooler 42 comprises at least one heat exchanger utilizing refrigerated water supplied at a temperature of between about 2° C. and 10° C. (35.5° F. and 50° F.) as the cooling medium. Finishing column overhead condensate stream 43 is preferably maintained at a temperature of 50° C. or lower, and more preferably 40° C. or lower.

At least a portion of subcooled finishing column overhead condensate stream 43 is passed, via line 4, to dehydration column heater/reboiler 12. A portion of subcooled finishing column overhead condensate stream 43 may optionally be returned to separatory vessel 40 via optional line 44. If present, optional line 44 may further comprise a flow control valve. As previously described, a portion of subcooled finishing column overhead condensate stream 43 is supplied to liquid jet eductor nozzle 47a as liquid stream 45. In at least one embodiment, finishing column overhead stream 8 has a dewpoint temperature of not more than 145 C and liquid stream 45 is supplied to liquid jet eductor nozzle 47a at a temperature of not more than 144.5° C. In at least one embodiment, liquid stream 45 is supplied to liquid jet eductor nozzle 47a at a temperature of between 10° C. and 100° C., preferably between 20° C. and 80° C. By using the condensate 45 to feed the liquid jet eductor, the use of water can be avoided in the system and a wastewater stream can be avoided. When used in a solvent-free acrylic acid production process such as the process disclosed in U.S. Pat. No. 8,242,308, the addition of water throughout the entire process can be avoided. The potential for polymer formation in the overhead piping and equipment of finishing column 17 may also be minimized by using the condensate 45 to cool overhead stream 8.

In at least one embodiment, the vacuum in finishing column 17 may be modulated by varying the volume of liquid in liquid stream 45.

It is preferred that an inhibitor package be added to one or more points within the finishing column overhead ADC condenser system. In at least one embodiment, an inhibitor package is added directly into separatory vessel 40. In other embodiments, an inhibitor package may be added to liquid stream 45 at a point upstream of the liquid jet eductor nozzle 47a. If added, the inhibitor package may comprise one or more of 4-hydroxy TEMPO (4HT), soluble manganese ions, soluble copper ions, hydroquinone (HQ), monomethyl ether of hydroquinone (MeHQ), and phenothiazine (PTZ).

In at least one embodiment, the finishing column 17 may further comprise a vacuum surface-condenser (not shown) through which vapor side product stream 5 is withdrawn and condensed. The vacuum surface-condenser vapor outlet may be connected to the vapor suction port 47b of the liquid jet eductor in the finishing column overhead ADC system.

In at least one alternative embodiment, the finishing column 17 may comprise a side draw ADC condenser system through which vapor side draw product stream 5 is withdrawn and condensed. In various embodiments of the present invention, the finishing column may comprise an overhead ADC condenser system, a side draw ADC condenser system, or both an overhead ADC condenser system and a side draw ADC condenser system.

In accordance with at least one embodiment, the overhead ADC condenser system may comprise a plurality of liquid jet eductors, a plurality of liquid-vapor separatory vessels, and/or a plurality of condensate coolers operated in series or parallel.

Although the ADC condenser systems have been described above in a two-column, solvent-free acrylic acid production process, the ADC condenser system may be used in other processes which produce a gaseous reaction mixture to reduce the amount of water and steam used in the process, thus reducing the amount of wastewater produced. Thus, another aspect of the present disclosure relates to improving processes for the recovery of (meth)acrylic acid from a gaseous reaction mixture comprising at least partially condensing a finishing column overhead stream using an aspirating direct contact condenser system to form a finishing column overhead condensate. The improvement may be applied to processes using two or three columns, as well as solvent-free processes and processes using a solvent, including azeotropic solvents.

Start-up processes for separation processes using an ADC condenser system differ from other processes. International Patent Application No. WO 2009/123872, which is incorporated by reference in its entirety, generally teaches the start-up of a separations process. To initially start-up a separations process comprising a finishing column overhead ADC condenser system, it will first be necessary to provide an initial liquid volume to separatory vessel 40. In such a case, the initial liquid volume may be actual process material produced in another apparatus, such as for example ester grade acrylic acid product or technical grade acrylic acid product. Alternatively, the initial liquid volume may be a synthetic mixture comprising acrylic acid and optionally one or more additional materials such as, for example, water, acetic acid, and polymerization inhibitors. Once an initial liquid volume is provided to separatory vessel 40, circulation of liquid from separatory vessel 40 to liquid jet eductor nozzle 47a may be initiated, thereby establishing an aspirating suction upon finishing column 17 that may be further modulated to control the pressure within the finishing column. When a continuous circulation has been established between overhead separatory vessel 40 and liquid jet eductor nozzle 47*a*, and the desired pressure within finishing column 17 has been achieved, finishing column 17 will be ready for the introduction of dehydration bottoms stream 3 when it becomes available.

Similarly, if the separations process to be initially started-up comprises a side draw ADC condensing system, an initial liquid volume comprising acrylic acid is preferably provided to said side draw ADC condensing system and a circulation of said initial liquid volume between the side draw separatory vessel and the side draw liquid jet eductor inlet nozzle must be established in order to draw in finishing column vapor side draw product stream 5 when it becomes available.

Although the invention is described above in considerable detail, this detail is for the purpose of illustration. Many variations and modifications can be made on the invention without departing from its spirit and scope as described in the following claims. All publications identified above, specifically including all U.S. patents, allowed patent applications, and published U.S. patent applications, are incorporated in their entirety herein by reference.

I claim:

1. A process for the recovery of (meth)acrylic acid using coupled distillation columns comprising a dehydration column that is coupled to a finishing column such that a tails stream from the dehydration column is fed directly or indirectly into a top of the finishing column while an overhead stream of the finishing column is fed directly or indirectly into a base of the dehydration column, the process comprising:
   A. dehydrating a gaseous reaction mixture comprising (meth)acrylic acid in said dehydration column to produce a dehydration column overhead stream and a dehydration column bottoms stream, wherein the dehydrating step is carried out without using azeotropic solvent;
   B. passing at least a portion of the dehydration column bottoms stream to the upper half of said finishing column;
   C. subjecting the portion of the bottoms stream passed to the finishing column to distillation at less than atmospheric pressure within the finishing column to produce at least a finishing column overhead stream and a finishing column bottoms stream;
   D. at least partially condensing the finishing column overhead stream using an overhead aspirating direct contact (ADC) condenser system to form a finishing column overhead condensate, and passing at least a portion of the finishing column overhead condensate to the dehydration column, wherein said ADC condenser system at least partially condenses the finishing column overhead stream and comprises at least one liquid jet eductor supplied with condensate from the finishing column overhead stream to generate a vacuum; at least one liquid-vapor separatory vessel; and at least one condensate cooler;
   E. collecting (meth)acrylic acid from the finishing column; wherein said (meth)acrylic acid collected is technical grade containing at least 98.5% by weight (meth) acrylic acid, less than 0.5% water, and less than 0.4% acetic acid, and without producing a wastewater stream.

2. The process of claim 1, wherein the finishing column is operated at a pressure of not more than 100 mmHg.

3. The process of claim 1, wherein said liquid-vapor separatory vessel is a centrifugal separator.

4. The process of claim 1, wherein said at least one condensate cooler is selected from the group consisting of a shell-and-tube heat exchanger, a spiral heat exchanger, a monolithic block exchanger, a jacketed pipe, and a plate-and-frame heat exchanger.

5. The process of claim 1, further comprising cooling said finishing column overhead condensate in said condensate cooler to a temperature of 50° C. or lower.

6. The process of claim 1 further comprising introducing an inhibitor package at one or more points within said overhead aspirating direct contact condenser system.

7. The process of claim 6, wherein the inhibitor package comprises one or more of 4-hydroxy TEMPO (4HT), soluble manganese ions, Hydroquinone (HQ), monomethyl ether hydroquinone (MeHQ), and phenothiazine (PTZ).

8. The process of claim 1, further comprising recovering a side draw product stream from the finishing column.

9. The process of claim 8, wherein the side draw product stream is a vapor-phase side draw product stream, the process further comprises at least partially condensing said vapor-phase side draw product stream from the finishing column using a side draw aspirating direct contact condenser system.

10. The process of claim 9, wherein said side draw aspirating direct contact condenser system comprises:
    A. at least one liquid jet eductor;
    B. at least one liquid-vapor separatory vessel; and
    C. at least one condensate cooler.

11. The process of claim 1, further comprising adding oxygen-containing gas to the finishing column.

12. The process of claim 1, wherein the overhead aspirating direct contact condenser system forms an overhead aspirating direct contact condenser system non-condensables vent stream, and at least a portion of the overhead aspirating direct contact condenser system non-condensables vent stream is transferred to the dehydration column.

13. The process of claim 1, wherein the overhead aspirating direct contact condenser system forms an overhead aspirating direct contact condenser system non-condensables vent stream, and at least a portion of the overhead aspirating direct contact condenser system non-condensables vent stream is transferred to a thermal oxidizer.

14. The process of claim 1, wherein the overhead aspirating direct contact condenser system forms an overhead aspirating direct contact condenser system non-condensables vent stream, and at least a portion of the overhead aspirating direct contact condenser system non-condensables vent stream is transferred to a vapor suction port of the at least one liquid jet eductor to regulate the pressure within the finishing column.

15. A process for producing technical grade (meth)acrylic acid containing at least 98.5% by weight (meth)acrylic acid, less than 0.5% water, and less than 0.4% acetic acid, the process comprising:
    A. forming a gaseous reaction mixture comprising (meth) acrylic acid through the gas-phase oxidation of at least one (meth)acrylic acid precursor;
    B. cooling the gaseous reaction mixture;
    C. using coupled distillation columns comprising a dehydration column that is coupled to a finishing column such that a tails stream from the dehydration column is fed directly or indirectly into a top of the finishing column while an overhead stream of the finishing column is fed directly or indirectly into a base of the dehydration column, dehydrating the cooled gaseous reaction mixture in said dehydration column to produce a dehydration column overhead stream and a dehydration column bottoms stream, wherein the dehydrating is carried out without using an azeotropic solvent;

D. at least partially condensing the dehydration column overhead stream to form a condensate, and returning at least a portion of the condensate to the dehydration column as reflux;

E. dividing the dehydration column bottoms stream into at least first and second dehydration column bottom streams, and passing at least a portion of one of the first and second dehydration column bottoms stream to a dehydration column heater/reboiler and passing at least a portion of the other dehydration column bottoms stream to the upper half of said finishing column;

F. subjecting the portion of the bottoms stream passed to the finishing column to distillation at less than atmospheric pressure within the finishing column to produce at least a finishing column overhead stream and a finishing column bottoms stream comprising heavy components;

G. at least partially condensing the finishing column overhead stream using an overhead aspirating direct contact (ADC) condenser system to form a finishing column overhead condensate and an overhead aspirating direct contact condenser system non-condensables vent stream, and passing at least a portion of the finishing column overhead condensate to the dehydration column heater/reboiler, wherein said ADC condenser system at least partially condenses the finishing column overhead stream and comprises at least one liquid jet eductor supplied with condensate from the finishing column overhead stream to generate a vacuum, at least one liquid-vapor separatory vessel and at least one condensate cooler; and H. passing at least a portion of the finishing column bottoms stream to a finishing column heater/reboiler, wherein the process produces (meth)acrylic acid without producing a wastewater stream.

16. The process of claim 15, wherein forming a gaseous reaction mixture comprising (meth)acrylic acid through the gas-phase oxidation of at least one (meth)acrylic acid precursor comprises the catalytic oxidation of acrolein.

17. The process of claim 16, wherein at least a portion of said acrolein is produced via the oxidation of propylene.

18. The process of claim 16, wherein at least a portion of said acrolein is produced via the oxydehydrogenation of propane.

19. The process of claim 15, wherein forming a gaseous reaction mixture comprising (meth)acrylic acid through the gas-phase oxidation of at least one (meth)acrylic acid precursor comprises the catalytic oxidation of methacrolein.

20. The process claim 19, wherein at least a portion of said methacrolein is produced via the oxidation of isobutylene and/or tert-butanol.

21. The process of claim 19, wherein at least a portion of said methacrolein is produced via the oxydehydrogenation of butane and/or isobutane.

22. The process of claim 15, wherein forming a gaseous reaction mixture comprising (meth)acrylic acid through the gas-phase oxidation of at least one (meth)acrylic acid precursor comprises the catalytic dehydration of at least one bio-material.

23. The process of claim 22, wherein said at least one bio-material is chosen from glycerol, 3-hydroxypropionic acid, and 2-hydroxypropanoic acid.

* * * * *